United States Patent [19]

Kainuma et al.

[11] Patent Number: 4,591,560
[45] Date of Patent: May 27, 1986

[54] PROCESS FOR SACCHARIFICATION OF STARCH USING ENZYME PRODUCED BY FUNGUS BELONGING TO GENUS CHALARA

[75] Inventors: Keiji Kainuma; Shoichi Kobayashi, both of Sakura, Japan

[73] Assignee: Director of National Food Research Institute Ministry of Agriculture, Forstry and Fisheries, Yatabe, Japan

[21] Appl. No.: 566,499

[22] Filed: Dec. 29, 1983

[30] Foreign Application Priority Data

Jan. 17, 1983 [JP] Japan .................................. 58-5564

[51] Int. Cl.$^4$ .................. C12P 19/20; C12P 19/14; C12N 9/30; C12N 9/34; C12R 1/645
[52] U.S. Cl. ..................................... 435/96; 435/99; 435/203; 435/205; 435/911
[58] Field of Search ................ 435/99, 96, 201, 202, 435/203, 911, 254, 255, 205

[56] References Cited

U.S. PATENT DOCUMENTS

| | | | |
|---|---|---|---|
| 3,697,378 | 10/1972 | Smalley | 435/99 |
| 4,061,541 | 12/1978 | Boyer et al. | 435/99 X |
| 4,113,509 | 9/1978 | Leach et al. | 435/99 X |
| 4,234,686 | 11/1980 | Marshall | 435/99 X |
| 4,540,663 | 9/1985 | Witt | 435/99 |

*Primary Examiner*—Thomas G. Wiseman
*Assistant Examiner*—Jayme A. Huleatt
*Attorney, Agent, or Firm*—Frishauf, Holtz, Goodman & Woodward

[57] ABSTRACT

A process for the saccharification of starch, which comprises saccharifying a raw and/or gelatinized starch by the use of an amylase produced by a fungus belonging to genus Chalara to produce glucose.

According to the process of the present invention, the starch is directly saccharified, and glucose can be obtained efficiently.

10 Claims, 5 Drawing Figures

PROCESS FOR SACCHARIFICATION OF STARCH USING ENZYME PRODUCED BY FUNGUS BELONGING TO GENUS CHALARA

BACKGROUND OF THE INVENTION

In the usual saccharification of starch, starch is once cooked to gelatinize, this gelatinized starch is liquefied by the action of α-amylase and, thereafter, glucoamylase is added to produce dextrose. This method, however, requires a large amount of energy for gelatinizing the starch prior to its saccharification. In order to minimize such energy consumption, extensive researches have been made particularly in recent years for amylase which can be applied directly to raw starch, that is, is capable of hydrolyzing directly the raw starch.

Such energy-saving starch saccharification is essential for the production of alcohol fuel from various starches as biomass sources. In connection with the alcoholic fermentation of raw starch, investigations by S. Ueda et al., Hayashida et al., Y. K. Park et al., and so on are known. S. Ueda et al. have long studied the alcoholic fermentation of raw starch using glucoamylase produced by Black Aspergillus, *Asp. awamori* (see S. Ueda & Y. Koba, *J. Fermentation Technology*, 58, No. 3, 237 (1980), and S. Ueda et al., *Biotech. Bioeng.*, Vol. 23, 291 (1981)). Hayashida et al. report that amylase produced by *Asp. awamori* is more effective in the hydrolysis of raw starch than amylase produced by *Asp. oryzae* or malt amylase. Y. K. Park et al. report the studies on the alcohol fermentation of starch without gelatinizing starch, using glucoamylase produced by *Aspergillus niger* or *Aspergillus awamori* (see *Biotech. Bioeng.*, 24, 495 (1982).

In the saccharification of raw starch using glucoamylases produced by *Aspergillus niger, Aspergillus awamori*, or fungus belonging to genus Rhizopus, some problems still remain unsolved. The most serious problem is that the rate of hydrolysis of raw starch of the above-described enzymes are seriously low compared with their rate of hydrolysis of gelatinized starch. In other words, their raw starch-hydrolyzing activity is seriously low although they have high enzymatic activity. Usually it is considered that enzymes capable of hydrolyzing raw starch at a rate of hydrolysis of about 1/30 of that for gelatinized starch are promising as raw starch-hydrolyzing enzymes (see S. Ueda, Workshop, *Carbohydrate Sources and Biotechnology*, page 25 (1982), held under the auspices of National Food Research Institute, Japan and sponsored by The United Nations University).

About 2,000 strains of microorganisms living in soil and on wood were isolated by us and examined to find those microorganisms satisfying the requirement that the ratio of the gelatinized starch-hydrolyzing degree to the raw starch-hydrolyzing degree is 10:1 or less. It has been found that some microorganisms satisfy the foregoing requirement. They are strains belonging to genus Chalara, and the properties of the enzymes secreted by them are similar to those of glucoamylases in respect of the mechanisms of enzyme reactions. These enzymes are active and stable in a slightly acidic region and have greatly higher raw starch-hydrolyzing activity compared with conventional glucoamylases; that is, the ratio of the gelatinized starch-hydrolyzing activity to the raw starch-hydrolyzing activity is from 3.5:1 to 5:1, which is greatly higher compared with those of the known glucoamylases. Hence it has been found that the saccharification of raw starch can be performed advantageously on a commercial scale by using the above-described enzymes.

SUMMARY OF THE INVENTION

The present invention relates to a process for the saccharification of starch (raw or gelatinized), characterized by saccharifying a starch by the use of an amylase produced by a fungus belonging to genus Chalara to produce dextrose directly.

DETAILED DESCRIPTION OF THE INVENTION

Figure 1:
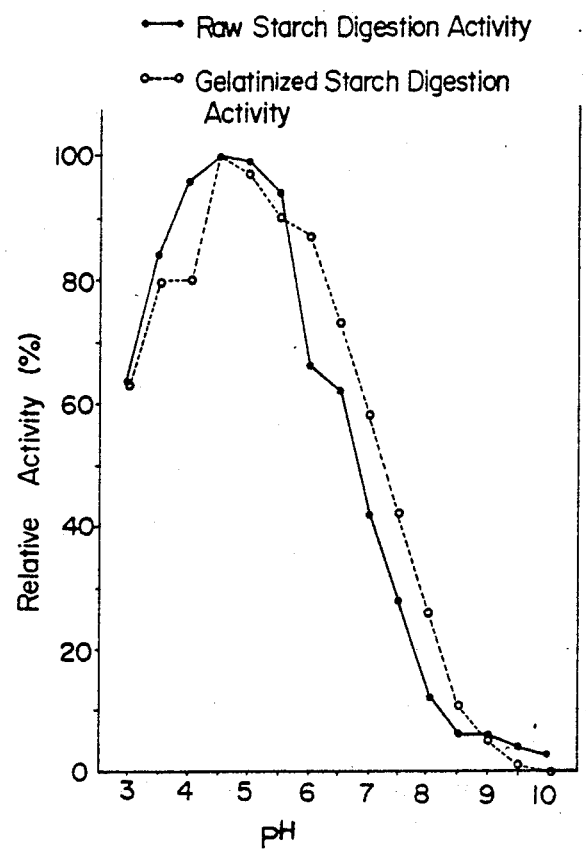
FIG. 1 is a curve showing activities at different pH values of a crude enzyme produced by *Chalara paradoxa* PNS-80 of the invention, said activity being indicated as relative value of raw starch-hydrolyzing activity to gelatinized starch-hydrolyzing activity; said activities are determined by incubating said enzyme with corn starch (raw starch) at 30° C. for 30 minutes or by incubating said enzyme with soluble starch (gelatinized starch) at 40° C. for 30 minutes. It discloses that activity is present over the range of pH of from about 3.5 to 9.5 and good results are obtained up to a pH of about 7, with best results obtained from about 3.5 to 6.

Any fungi belonging to genus Chalara and having an ability to produce enzyme of high raw starch-hydrolyzing ability can be used in the invention. A typical example is a strain *Chalara paradoxa* PNS-80. Its microbiological characteristics as determined based on K. Tsubaki and S. Udagawa, A PICTURE BOOK OF FUNGI (last volume), Kodansha Life Scientific Publishers are as follows:

(I) Morphological Characteristics (a) It forms conidiophores growing vertically from hyphae, which have a long cylindrical form and 2 to 3 septa.

(b) It forms phialo type conidia which are cylindrical or barrel-like in shape and have an average size of 12 microns × 4 microns.

(c) It forms brown or gray-black thick wall spores, the skin layer of which is covered with a smooth or irregular external wall.

(II) Culture Characteristics (a) It grows on a malt agar medium in the form of gray or gray-yellow flocculence. At a later stage of the growth, it further becomes dark.

(b) It grows on a medium comprising 1% soluble starch, 1% polypeptone, and 0.7% bouillon in the same flocculent form as in (a) above.

In view of the above-described morphological and culture characteristics, it is reasonable to identify the strain as *Chalara paradoxa*. This strain has been deposited in the Fermentation Research Institute under the accession number of FERM BP-422.

The desired enzymes can be prepared by cultivating the fungus belonging to genus Chalara by the usual aerobic liquid cultivation or cultivation aerated with agitation. For this purpose, various culture media can be used. As a carbon source, raw starch from corn, potato, sweet potato, tapioca, waxy corn, rice, wheat, sago, high-amylose corn and so forth, and a starch hydrolyzate of DE 10-25 are preferred to use in a proportion of from 2 to 7%, since the desired enzymes are induced using raw starch. As a nitrogen source, peptone, meat extract, corn steep liquor, peptide-containing compounds, and so forth can be used singly or in combination with each other. If desired, small amounts of inorganic salts, such as NaCl, $FeSO_4$, $Ba(OH)_2$, $FeCl_3.6H_2O$, $SrCl_2.6H_2O$, LiCl, $MgSO_4.7H_2O$, and $MnSO_4.5H_2O$, can be added.

The thus-prepared culture medium is inoculated with the above-described strain, which is then cultivated under aerobic conditions at pH 4–8.5 at 25°–40° C. for 24–96 hours, whereby the desired enzyme can be accumulated therein.

The enzyme used in the present process may be utilized when still part of the culture broth obtained by cultivating the amylase-producing microorganism belonging to genus Chalara on a nutrient medium in the manner described above, in the form of its filtrate, in the form of a concentrated filtrate, and in the form of a purified enzyme prepared from the filtrate.

Separation and purification of the present enzyme can be performed by the known procedures which have been widely used in the separation and purification of enzymes from their culture broth. For example, a method of concentrating the filtrate under reduced pressure or by ultrafiltration, a method of salting out with compounds such as ammonium sulfate, sodium sulfate and sodium chloride, a specific adsorption method utilizing raw starch, a fractional precipitation method using compounds such as methanol, ethanol and acetone, a chromatographic method using DEAE-Sephadex and an ion exchange resin, an isoelectric point precipitation method, and an electric dialysis method can be used singly or in combination with each other.

The activity of the enzyme is measured as follows:

A mixture of 20 milligrams of raw corn starch, 0.2 milliliter of a 0.1 M acetate buffer (pH: 4.5), 0.2 milliliter of an enzyme solution, and 1.6 milliliters of deionized water is incubated at 40° C. for 30 minutes. At the end of the time, the amount of glucose formed is measured by the Somogyi-Nelson method. One unit of enzyme activity is defined as the amount of enzyme which produces 1 micromole (180 micrograms) of glucose per minute under the conditions as described above.

The gelatinized starch-hydrolyzing activity is determined by measuring the amount of reducing sugar formed when the same experiment as above is performed using 0.25 milliliter of a 2% soluble starch solution. One unit of the activity is defined in the same manner as above.

The physical and chemical properties of the present enzyme are shown below. This enzyme is the one isolated by ultra filtration of the culture filtrate.

(1) Action and Substrate Specificity

The present enzyme is capable of hydrolyzing raw and gelatinized starches from corn, potato, rice, sweet potato, waxy corn, sago and tapioca, yielding reducing sugar. Paper chromatography and high-pressure liquid chromatography analyses of the reducing sugar show that oligosaccharides including disaccharide are not formed and glucose is formed and accumulated from the initial stage of the reaction. It is believed, therefore, that the present enzyme is a glucoamylase which converts starch into glucose by an exo-type reaction.

(2) Optimum pH and Stable pH Range

Figure 2:
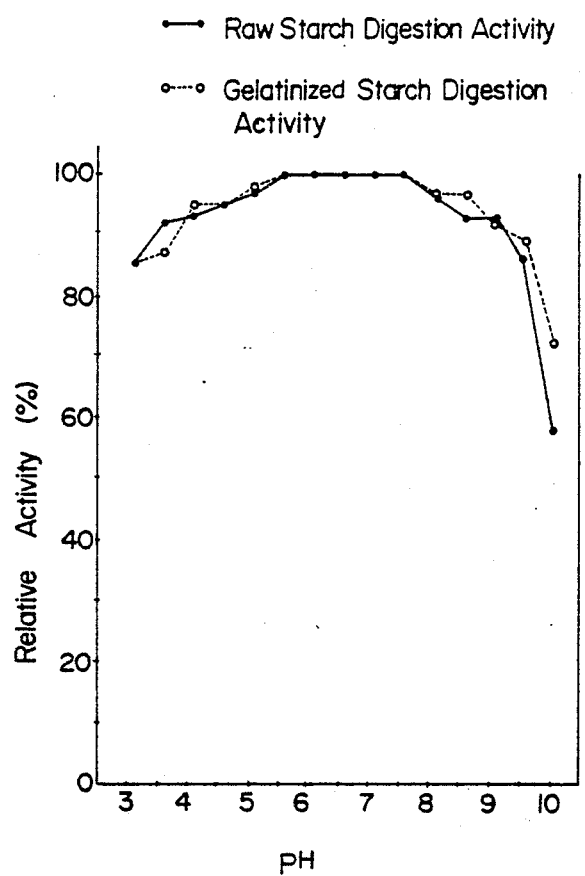
FIG. 2 is a pH stability curve (over the range of 3–9.5) as determined by measuring the residual activity of an enzyme solution after its treatment at 40° C. for 30 minutes, provided that the measurement conditions are the same as in FIG. 1.

The optimum pH and stable pH range were determined by applying a 0.2 M acetate buffer (pH: 3–5.0), a trismalate buffer (pH: 5.5–8.5), and a sodium carbonate buffer (pH: 9.0–10.0) to raw starch at 40° C. for 30 minutes. The results are shown in FIGS. 1 and 2.

(3) Optimum Temperature and Temperature Stability

Figure 3:
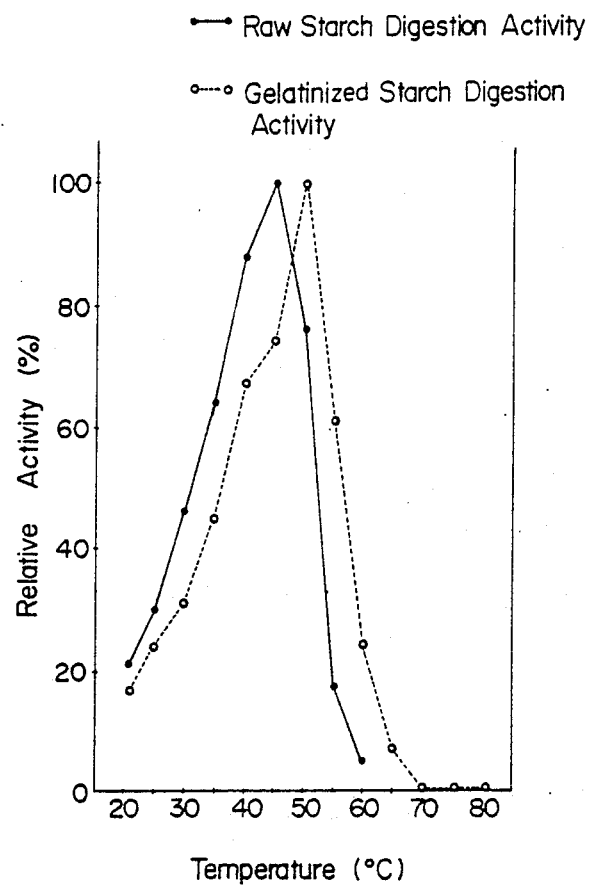
FIG. 3 is a curve showing the optimum temperature of the present enzyme produced by *Chalara paradoxa* PNS-80, which is obtained by plotting relative enzyme activities as determined by incubating said enzyme with starch at a predetermined temperature for 30 minutes. It further discloses a broad temperature range when using raw starch of about 30° to 50° C. and that best results for raw starch are obtained at temperatures of about 40° to 48° C.
Figure 4:
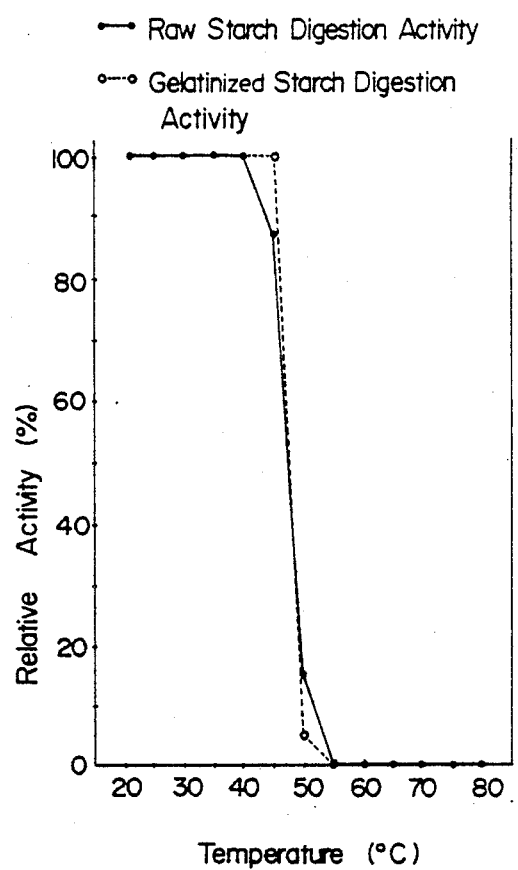
FIG. 4 shows temperature stability of the present enzyme produced by *Chalara paradoxa* PNS-80, and it is obtained by plotting the residual activity of an enzyme solution after its treatment at a predetermined temperature for 30 minutes.

The optimum temperature was determined by measuring the formed reducing sugar after 30 minutes incubation with soluble starch solution, and temperature stability were determined by the remaining enzyme activity after its treatment for 30 minutes at different temperatures. Experimental results obtained using gelatinized soluble starch as a substrate are shown in FIGS. 3 and 4. Since the present enzyme is intended to apply to raw starch, it is used within the stable temperature range thereof.

(4) Influences of Coexisting Ions

Addition of calcium (Ca) ion increases the thermal stability of the gelatinized starch-hydrolyzing activity by about 5° C.

Glucose can be formed by application of the present enzyme to raw starch and/or gelatinized starch.

Strains capable of producing the present enzyme include, as well as *Chalara paradoxa* PNS-80, *Chalara fusidioides, Chalara cylindrosperma, Chalara mycoderma, Chalara quercina* and *Chalara elegans*.

The present invention permits the direct saccharification of starch and, therefore, it provides a process for producing conveniently and efficiently useful substances such as alcohols from various starches such as biomass sources. In particular, the enzyme of the invention is suitable for industrial utilization because of its high raw starch-hydrolyzing activity.

The following Examples are for illustrative purposes only and are not meant to limit the invention set forth in the claims appended hereto.

EXAMPLE 1

One liter of a medium containing 65 grams of corn steep liquor, 7 grams of meat extract, 3 grams of sodium chloride, and 500 milligrams of ferrous sulfate (adjusted to pH 4.0) was placed in a 5-liter flask and sterilized. After sterilization, 40 grams of sago starch which had been subjected to dry air sterilization at 100° C. was added to the medium, which was then inoculated with one loop of slant culture of *Chalara paradoxa* PNS-80 (FERM BP-422). Shaking cultivation was performed at 30° C. for 5 days.

After the cultivation was completed, microorganisms and unreacted starch were removed by centrifugal separation, and a supernatant was used as a crude enzyme solution (raw starch-hydrolyzing activity: 1.0 International Unit (IU) per milliliter).

Granules, i.e. raw, waxy corn starch, corn starch, and wheat starch were placed in the respective Erlenmeyer flasks each in an amount of 2.5 grams. Then 25 milliliters of the enzyme solution as prepared above was added to each flask. Furthermore 25 milliliters of a 0.1 M acetate buffer (pH 4.5) and 200 milliliters of deionized water were added, and shaking cultivation was performed at 30° C.

The amount of glucose formed was measured by the Somogyi-Nelson method. The degree of hydrolysis of each starch after 24 hour reaction was as follows:
  Corn starch: 68%
  Waxy corn starch: 85.5%
  Wheat starch: 76.3%
Paper chromatography analysis shows that the sugar formed consisted of dextrose alone.

EXAMPLE 2

The same strain as used in Example 1 was cultivated on a medium consisting of 65 grams of corn steep liquor, 3 grams of sodium chloride, and 70 grams of tapioca which had been sterilized with radiation. After the cultivation was completed, 2 volumes of ethanol was added to one volume of the fermentation broth to precipitate an enzyme. To 50 milligrams of the precipitate were added 50 milliliters of a 0.1 M acetate buffer (pH 4.5) and 200 milliliters of deionized water.

Thereafter rice starch, potato starch, and sweet potato starch were hydrolyzed in the same manner as in Example 1. The degree of hydrolysis of each starch after 24 hour reaction was as follows:
  Rice starch: 89%
  Potato starch: 11%
  Sweet potato starch: 48.6%

EXAMPLE 3

One liter of a medium containing 65 grams of corn steep liquor, 7 grams of meat extract, 3 grams of sodium chloride, and 500 milligrams of ferrous sulfate (adjusted to pH 4.0) was placed in a 5-liter Erlenmeyer flask and sterilized. After the completion of sterilization, 70 grams of sago starch which had been sterilized with γ-ray radiation was added to the medium, which was then inoculated with one loop of slunt culture of the same strain as used in Example 1. Shaking cultivation was performed with shaking for 6 days.

After the cultivation was completed, the fermentation broth was subjected to centrifugal separation to obtain a supernatant. This supernatant was used as a crude enzyme solution (1.6 International Units per milliliters (IU/ml)) in the raw starch-hydrolyzing reaction as described below.

Rice starch, waxy corn starch, and wheat starch were placed in the respective Erlenmeyer flasks each in an amount of 5 grams. Then 25 milliliters of the enzyme solution as prepared above, 25 milliliters of a 0.1 M acetate buffer (pH 4.5), and 200 milliliters of deionized water were added to each flask. Shaking cultivation was performed at 30° C. for 48 hours.

The amount of glucose formed was measured by the Somogyi-Nelson method. The degree of hydrolysis of each starch was as follows:
  Rice starch: 86%
  Waxy corn starch: 86%
  Wheat starch: 86%.

EXAMPLE 4

The procedure of Example 3 was repeated wherein tapioca starch and sweet potato starch were used as the substrate in place of the rice starch, waxy corn starch, and wheat starch.

The degree of hydrolysis of each starch was as follows:
  Tapioca starch: 89.8%
  Sweet potato starch: 84%

EXAMPLE 5

The procedure of Example 3 was repeated wherein sago starch and potato starch were used as the substrate in place of the rice starch, waxy corn starch, and wheat starch.

The degree of hydrolysis of each starch was as follows:
  Sago starch: 52%
  Potato starch: 35%.

EXAMPLE 6

One liter of a medium containing 65 grams of corn steep liquor, 7 grams of meat extract, 3 grams of sodium chloride, and 300 milligrams of ferrous sulfate (adjusted to pH 4.0) and placed in a 5-liter flask and sterilized. After sterilization, 70 grams of sago starch which had been sterilized with radiation was added to the medium, which was then inoculated with one loop of slunt culture of the same strain as used in Example 1. Shaking cultivation was performed for 5 days. Microorganisms were removed by centrifugal separation, and a supernatant was used as a crude enzyme solution (activity for gelatinized starch: 14.9 International Units per milliliter (IU/ml); activity for raw starch: 1.6 International Units per milliliter (IU/ml)).

A mixture of 2.5 grams of each of the raw starches as described in the Table, 12.5 milliliters of a 0.1 M acetate buffer (pH 4.0), 100 milliliters of deionized water, and 12.5 milliliters of the crude enzyme solution as prepared above was incubated at 30° C. After 24 hours and 48 hours, the degree of hydrolysis of the starch was measured. The results are shown in the Table below.

TABLE

| Starch | Time | |
|---|---|---|
| | 24 hours | 48 hours |
| Rice starch | 95.0 | 96.1 |
| Waxy corn starch | 93.5 | 97.3 |
| Wheat starch | 91.5 | 96.2 |
| Corn starch | 90.9 | 95.6 |
| Tapioca | 81.2 | 99.8 |
| Sweet potato starch | 73.3 | 92.6 |
| Sago starch | 33.5 | 57.7 |
| Potato starch | 19.4 | 38.6 |

EXAMPLE 7

Figure 5:
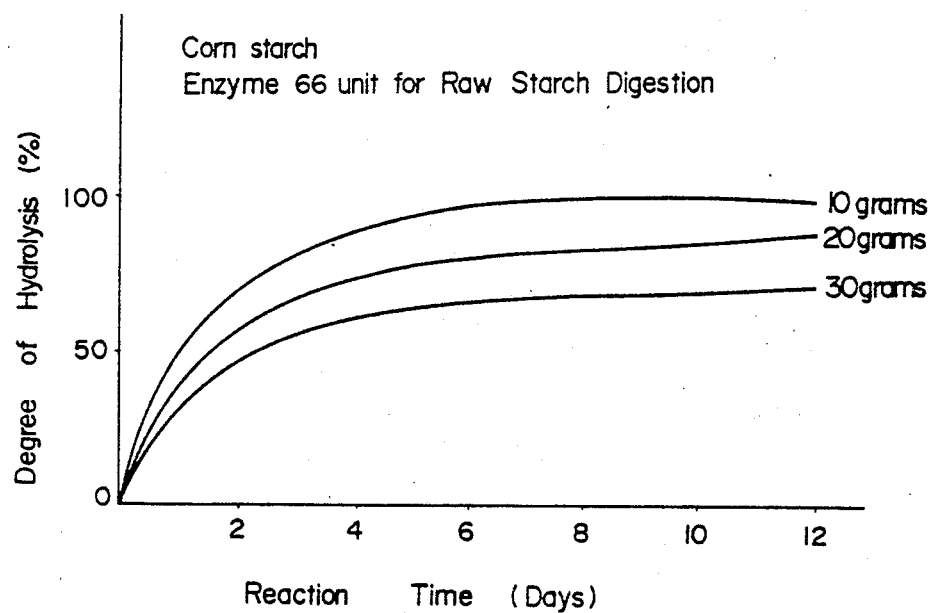
FIG. 5 is a raw corn starch-hydrolyzing curve as determined under the conditions described in Example 7.

A mixture of 42 milliliters of an enzyme solution as prepared in Example 6 (raw starch-hydrolyzing activity: 66 International Units in 40 milliliters (IU/ml)), 20 milliliters of a 0.1 M acetate buffer, and 38 milliliters of deionized water was prepared in a 500-milliliter flask. To this enzyme solution was added raw corn starch in an amount of 10 grams, 20 grams or 30 grams. The degree of hydrolysis at each amount was measured and plotted to obtain a hydrolysis curve as shown in FIG. 5. When the amount of the starch added was 10 grams, the degree of hydrolysis after 7 day incubation was 100%;

when the amount of the starch added was 20 grams, the degree of hydrolysis after 9 day incubation was 90%; and when the amount of the starch added was 30 grams, the degree of hydrolysis after 9 day incubation was 72%.

What is claimed is:

1. A process for the saccharification of starch to produce glucose, which comprises contacting a starch with an amylase produced by a fungus belonging to the genus Chalara to produce glucose in an aqueous medium having a pH of from 3 to 9.5 at a temperature of from 30° to 50° C. to produce said glucose, and recovering said glucose, said amylase has a pH stability of 3–9.5, an optimum temperature of 45° C. for raw starch and of 50° C. for gelatinized starch and thermostability of 45° C.

2. The process of claim 1, wherein said starch is a raw starch.

3. The process of claim 2, wherein said pH is up to 7 and said temperature is between 40° and 48° C.

4. The process of claim 3, wherein said pH is between about 3.5 and 6.

5. The process of claim 4, wherein said fungus belonging to the genus Chalara is *Chalara paradoxa* PNS-80 (FERM BP- 422).

6. The process of claim 1, wherein said fungus belonging to the genus Chalara is *Chalara paradoxa* PNS-80 (FERM BP- 422).

7. The process of claim 1, wherein said fungus belonging to the genus Chalara is selected from the group consisting of *Chalara quercina* and *Chalara elegans*.

8. The process of claim 1, wherein said aqueous medium also contains calcium ion.

9. A process for producing an amylase which has high activity in digesting starch to form glucose comprising cultivating *Chalara paradoxa* PNS-80 (FERM BP-422) in a culture medium containing a nitrogen source under aerobic conditions at a pH of 4–8.5 and at a temperature of 25°–40° C. to produce said amylase, said amylase has a pH stability of 3–9.5, an optimum temperature of 45° C. for raw starch and of 50° C. for gelatinized starch and thermostability of 45° C.

10. The process of claim 9, wherein said amylase is separated from said culture medium.

* * * * *